(12) United States Patent
Ashmore et al.

(10) Patent No.: US 8,168,231 B2
(45) Date of Patent: May 1, 2012

(54) ANTIMICROBIAL COMPOSITION USEFUL FOR PRESERVING WOOD

(75) Inventors: John William Ashmore, Lansdale, PA (US); Kiran Pareek, Bensalem, PA (US)

(73) Assignee: Rohm and Haas Company, Philadelphia, PA (US)

( * ) Notice: Subject to any disclaimer, the term of this patent is extended or adjusted under 35 U.S.C. 154(b) by 832 days.

(21) Appl. No.: 11/983,695

(22) Filed: Nov. 9, 2007

(65) Prior Publication Data

US 2008/0118575 A1 May 22, 2008

Related U.S. Application Data

(60) Provisional application No. 60/860,743, filed on Nov. 22, 2006.

(51) Int. Cl.
*A01N 59/20* (2006.01)
*A01N 43/80* (2006.01)
(52) U.S. Cl. ......... 424/638; 424/630; 514/372; 514/369

(58) Field of Classification Search ........................ None
See application file for complete search history.

(56) References Cited

U.S. PATENT DOCUMENTS

| | | | |
|---|---|---|---|
| 2004/0258767 A1* | 12/2004 | Leach et al. | 424/630 |
| 2005/0058689 A1* | 3/2005 | McDaniel | 424/426 |
| 2006/0112850 A1 | 6/2006 | Zhang et al. | |
| 2006/0147632 A1 | 7/2006 | Zhang et al. | |
| 2006/0251915 A1 | 11/2006 | Jin et al. | |

FOREIGN PATENT DOCUMENTS

| | | |
|---|---|---|
| EP | 864406 | 9/1998 |
| EP | 1733616 A | 12/2006 |
| JP | 2001150404 A | 8/2001 |
| WO | WO 91/11306 | 8/1991 |
| WO | WO 2006/044218 | 4/2006 |

* cited by examiner

*Primary Examiner* — David J Blanchard
*Assistant Examiner* — Barbara Frazier
(74) *Attorney, Agent, or Firm* — Kenneth Crimaldi

(57) ABSTRACT

Antimicrobial compositions useful for preserving wood, and comprising a variety of antimicrobial compounds.

2 Claims, No Drawings

ANTIMICROBIAL COMPOSITION USEFUL FOR PRESERVING WOOD

This application claims the benefit of priority under 35 U.S.C. §119(e) of U.S. Provisional Patent Application No. 60/860,743 filed on Nov. 22, 2006.

This invention relates to combinations of biocides useful for preserving wood, the combinations having greater activity than would be observed for the individual antimicrobial compounds.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, e.g., those resistant to some antimicrobial compounds. Combinations of different antimicrobial compounds are sometimes used to provide overall control of microorganisms in a particular end use environment. For example, EP 864,406 discloses a combination of 4,5-dichloro-2-n-octyl-4-isothiazolin-3-one and a monoethanolamine complex of copper, but this reference does not suggest the synergistic ratios claimed herein. Moreover, there is a need for additional combinations of antimicrobial compounds having enhanced activity against various strains of microorganisms to provide effective control of the microorganisms that is both quick and long lasting. The problem addressed by this invention is to provide such additional combinations of antimicrobial compounds.

STATEMENT OF THE INVENTION

The present invention is directed to a synergistic antimicrobial composition comprising: (a) monoethanolamine complex of copper(II); and (b) 4,5-dichloro-2-n-octyl-4-isothiazolin-3-one.

The present invention is further directed to a synergistic antimicrobial composition comprising: (a) 4,5-dichloro-2-n-octyl-4-isothiazolin-3-one; and (b) micronized copper.

DETAILED DESCRIPTION OF THE INVENTION

In this invention, copper(II) in a monoethanolamine complex preferably is in the form of a chloride, carbonate or bicarbonate. As used herein, the following terms have the designated definitions, unless the context clearly indicates otherwise. "DCOIT" is 4,5-dichloro-2-n-octyl-4-isothiazolin-3-one. "Micronized copper" is an inorganic copper(II) salt which has been ground to less than 1 micron average particle size. Suitable copper(II) salts for micronized copper include, e.g., cupric oxide, copper hydroxide, copper carbonate and basic copper carbonate. The term "antimicrobial compound" refers to a compound capable of inhibiting the growth of or controlling the growth of microorganisms at a locus; antimicrobial compounds include bactericides, bacteristats, fungicides, fungistats, algaecides and algistats, depending on the dose level applied, system conditions and the level of microbial control desired. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter, ATCC=American Type Culture Collection, and MIC=minimum inhibitory concentration. Unless otherwise specified, temperatures are in degrees centigrade (° C.), and references to percentages (%) are by weight. Percentages of antimicrobial compounds in the composition of this invention are based on the total weight of active ingredients in the composition, i.e., the antimicrobial compounds themselves, exclusive of any amounts of solvents, carriers, dispersants, stabilizers or other materials which may be present. For copper-containing biocides, the active ingredient is calculated as copper metal.

In one embodiment of the invention, the antimicrobial composition comprises monoethanolamine complex of copper(II) and 4,5-dichloro-2-n-octyl-4-isothiazolin-3-one. Preferably, a weight ratio of monoethanolamine complex of copper(II) to 4,5-dichloro-2-n-octyl-4-isothiazolin-3-one is from 1:0.0002 to 1:0.1176. Another preferred weight ratio is from 1:0.0013 to 1:0.1176.

In another embodiment of the invention, the antimicrobial composition comprises 4,5-dichloro-2-n-octyl-4-isothiazolin-3-one and micronized copper. Preferably, a weight ratio of 4,5-dichloro-2-n-octyl-4-isothiazolin-3-one to micronized copper is from 1:48 to 1:125,000. Another preferred weight ratio is from 1:59 to 1:125,000.

The antimicrobial compounds in the composition of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, benzyl alcohol, phenethyl alcohol and phenoxypropanol; ketones, such as acetone and methyl ethyl ketone; esters, such as ethyl acetate, butyl acetate, glycerol triacetate, TEXANOL (2,2,4-trimethyl-1,3-pentanediol, mono-isobutyrate ester; available from Eastman Co., Kingsport Tenn.), and methyl and isobutyl esters of $C_3$-$C_7$ dicarboxylic acids, e.g., succinic, glutaric and adipic acids; carbonates, such as propylene carbonate and dimethyl carbonate; and mixtures thereof. It is preferred that the solvent is selected from water, glycols, glycol ethers, esters and mixtures thereof. Suitable solid carriers include, for example, cyclodextrin, silicas, diatomaceous earth, waxes, cellulosic materials, alkali and alkaline earth (e.g., sodium, magnesium, potassium) metal salts (e.g., chloride, nitrate, bromide, sulfate) and charcoal.

When an antimicrobial component is formulated in a solvent, the formulation may optionally contain surfactants. When such formulations contain surfactants, they are generally in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art. U.S. Pat. No. 5,444,078 may be consulted for further general and specific details on the preparation of various microemulsions and microemulsive concentrates.

An antimicrobial compound also can be formulated in the form of a dispersion. The solvent component of the dispersion can be an organic solvent or water, preferably water. Such dispersions can contain adjuvants, for example, co-solvents, thickeners, anti-freeze agents, dispersants, fillers, pigments, surfactants, biodispersants, sulfosuccinates, terpenes, furanones, polycations, stabilizers, scale inhibitors and anti-corrosion additives.

The antimicrobial compounds may be formulated separately or together. When both antimicrobial compounds are each first formulated with a solvent, the solvent used for the first antimicrobial compound may be the same as or different from the solvent used to formulate the other commercial antimicrobial compound. It is preferred that the two solvents are miscible. In the alternative, the first antimicrobial compound and the other antimicrobial compound may be combined directly and then a solvent added to the mixture.

Those skilled in the art will recognize that the antimicrobial compounds of the present invention may be added to a locus sequentially, simultaneously, or may be combined before being added to the locus. It is preferred that the first antimicrobial compound and the second antimicrobial compound be added to a locus simultaneously or combined prior to being added to the locus. When the antimicrobial compounds are combined prior to being added to a locus, such combination may optionally contain adjuvants, such as, for example, solvent, thickeners, anti-freeze agents, colorants, sequestrants (such as ethylenediamine, tetraacetic acid, ethylenediaminedisuccinic acid, iminodisuccinic acid and salts thereof), dispersants, surfactants, biodispersants, sulfosuccinates, terpenes, furanones, polycations, stabilizers, scale inhibitors and anti-corrosion additives.

The antimicrobial compositions of the present invention can be used to inhibit the growth of microorganisms by introducing an antimicrobially effective amount of the compositions onto, into, or at a locus subject to microbial attack. Suitable loci include, for example: cooling towers; air washers; mineral slurries; wastewater treatment; ornamental fountains; reverse osmosis filtration; ultrafiltration; ballast water; evaporative condensers; heat exchangers; pulp and paper processing fluids; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos, soaps; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas.

Preferably, the antimicrobial compositions of the present invention are used to inhibit the growth of microorganisms at a locus selected from one or more of wood and wood products, emulsions, dispersions, paints, latices, household products, cosmetics, toiletries, shampoos, soaps, detergents, machining fluids and industrial cleaners. In particular, the antimicrobial compositions are useful in wood and wood products, emulsions, dispersions, paints and latices.

When the synergistic compositions of the present invention are used in personal care compositions, the formulated compositions may also comprise one or more ingredients selected from UV radiation-absorbing agents, surfactants, rheology modifiers or thickeners, fragrances, moisturizers, humectants, emollients, conditioning agents, emulsifiers, antistatic aids, pigments, dyes, tints, colorants, antioxidants, reducing agents and oxidizing agents.

The specific amount of the composition of this invention necessary to inhibit or control the growth of microorganisms in a locus depends upon the particular locus to be protected. Typically, the amount of the composition of the present invention to control the growth of microorganisms in a locus is sufficient if it provides from 0.1 to 25,000 ppm active ingredient of the composition in the locus. It is preferred that the active ingredients of the composition be present in the locus in an amount of at least 0.5 ppm, more preferably at least 1 ppm, more preferably at least 10 ppm and most preferably at least 50 ppm. In one embodiment of the invention, the active ingredients are present in an amount of at least 500 ppm. It is preferred that the active ingredients of the composition be present in the locus in an amount of no more than 20,000 ppm, more preferably no more than 15,000 ppm, more preferably no more than 10,000 ppm. In one embodiment of the invention, the active ingredients are present in an amount of no more than 10,000 ppm, more preferably no more than 7,500 ppm, and most preferably no more than 5,000 ppm.

EXAMPLES

The synergism of the combination of the present invention was demonstrated by testing a wide range of concentrations and ratios of the compounds.

One measure of synergism is the industrially accepted method described by Kull, F. C.; Eisman, P. C.; Sylwestrowicz, H. D. and Mayer, R. L., in *Applied Microbiology* 9:538-541 (1961), using the ratio determined by the formula:

$$C_a/C_A + C_b/C_B = \text{Synergy Index ("SI")}$$

wherein:
$C_A$=concentration of compound A (first component) in ppm, acting alone, which produced an end point (MIC of Compound A).
$C_a$=concentration of compound A in ppm, in the mixture, which produced an end point.
$C_B$=concentration of compound B (second component) in ppm, acting alone, which produced an end point (MIC of Compound B).
$C_b$=concentration of compound B in ppm, in the mixture, which produced an end point.

When the sum of $C_a/C_A$ and $C_b/C_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of an antimicrobial compound is the lowest concentration tested under a specific set of conditions that prevents the growth of added microorganisms.

Micronized copper used in these experiments was copper (II) hydroxide, with an average particle size less than one micron.

Synergy tests were conducted using standard microtiter plate assays with media designed for optimal growth of the test microorganism. Minimal salt medium supplemented with 0.2% glucose and 0.1% yeast extract (M9GY medium) was used for bacteria testing; Potato Dextrose Broth (PDB medium) was used for yeast and mold testing. In this method, a wide range of combinations of microbicides was tested by conducting high resolution MIC assays in the presence of various concentrations of biocides. High resolution MICs were determined by adding varying amounts of microbicide to one column of a microtitre plate and doing subsequent ten-fold dilutions using an automated liquid handling system to obtain a series of end points ranging of active ingredient. The synergy of the combinations of the present invention was determined against two bacteria, *Pseudomonas aeruginosa* (*Ps. aeruginosa*—ATCC # 9027) and *Staphylococcus aureus* (*S. aureus*—ATCC # 6538), a yeast, *Candida albicans* (*C. albicans*—ATCC # 10231), and a mold, *Aspergillus niger* (*A. niger*—ATCC 16404). The bacteria were used at a concentration of about $1\text{-}6 \times 10^6$ bacteria per mL and the yeast and mold at $1\text{-}5 \times 10^5$ fungi per mL. These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the microbicide combinations of the present invention are shown below in the Tables. Each table shows the specific combinations of Component (a) and the second component (b); results against the microorganisms tested with incubation times; the endpoint activity in ppm measured by the MIC for Component (a) ($C_a$), for the second component alone ($C_b$), for the mixture ($C_a$) and for second component in the mixture ($C_b$); the calculated SI value; and the range of synergistic ratios for each combination tested (first component/second component or a+b).

The following Tables summarize data for combinations of biocides against fungi and bacteria, along with their synergy index (SI) and the weight ratios of biocides. All amounts of biocides are reported as ppm of active ingredient.

TABLE 1

| Test Organisms | Contact Time | Ca | Cb | S.I. | Ca/Cb |
|---|---|---|---|---|---|
| A. niger ATCC # 16404 | 3 days | 300 | — | — | — |
| | | — | 0.25 | — | — |
| | | 30 | 0.125 | 0.60 | 1/.0042 |
| | | 50 | 0.125 | 0.67 | 1/.0025 |
| | | 60 | 0.125 | 0.70 | 1/.0021 |
| | | 80 | 0.125 | 0.77 | 1/.0016 |
| | | 100 | 0.125 | 0.83 | 1/.0013 |
| | | 200 | 0.125 | 1.17 | 1/.0006 |
| | 7 days | 300 | — | — | — |
| | | — | 0.25 | — | — |
| | | 300 | 0.015 | 1.06 | 1/.0001 |
| | | 300 | 0.007 | 1.03 | 1/.00002 |
| C. albicans ATCC # 10231 | 48 hrs | 200 | — | — | — |
| | | — | 1 | — | — |
| | | 20 | 0.5 | 0.60 | 1/.025 |
| | | 30 | 0.5 | 0.65 | 1/.0166 |
| | | 40 | 0.5 | 0.70 | 1/.0125 |
| | | 50 | 0.5 | 0.75 | 1/.01 |
| | | 60 | 0.5 | 0.80 | 1/.0083 |
| | | 80 | 0.5 | 0.90 | 1/.0063 |
| | | 100 | 0.5 | 1.00 | 1/.005 |
| | | 200 | 0.03 | 1.03 | 1/.0002 |
| | | 200 | 0.015 | 1.02 | 1/.0001 |
| | | 200 | 0.007 | 1.01 | 1/.00004 |
| | 72 hrs | 200 | — | — | — |
| | | — | 1 | — | — |
| | | 20 | 0.5 | 0.60 | 1/.025 |
| | | 30 | 0.5 | 0.65 | 1/.0167 |
| | | 40 | 0.5 | 0.70 | 1/.0125 |
| | | 50 | 0.5 | 0.75 | 1/.01 |
| | | 60 | 0.5 | 0.80 | 1/.0083 |
| | | 80 | 0.5 | 0.90 | 1/.0063 |
| | | 100 | 0.5 | 1.00 | 1/.005 |
| | | 200 | 0.03 | 1.03 | 1/.0002 |
| | | 200 | 0.015 | 1.02 | 1/.0001 |
| | | 200 | 0.007 | 1.01 | 1/.00004 |
| Ps. aeruginosa ATCC#9027 | 24 hrs | 120 | — | — | — |
| | | — | 3 | — | — |
| | | 17 | 2 | 0.81 | 1/.1176 |
| | | 21 | 2 | 0.84 | 1/.0952 |
| | | 26 | 2 | 0.88 | 1/.0769 |
| | | 35 | 2 | 0.96 | 1/.057 |
| | | 44 | 2 | 1.03 | 1/.0455 |
| | | 35 | 1 | 0.63 | 1/.0286 |
| | | 44 | 1 | 0.70 | 1/.0227 |
| | | 80 | 1 | 1.00 | 1/.0125 |
| | | 80 | 0.5 | 0.83 | 1/.0063 |
| | | 120 | 0.5 | 1.17 | 1/.0042 |
| | | 80 | 0.25 | 0.75 | 1/.0031 |
| | | 120 | 0.25 | 1.08 | 1/.0021 |
| | | 80 | 0.125 | 0.71 | 1/.0016 |
| | | 120 | 0.125 | 1.04 | 1/.001 |

TABLE 1-continued

| Test Organisms | Contact Time | Ca | Cb | S.I. | Ca/Cb |
|---|---|---|---|---|---|
| | | 120 | 0.06 | 1.02 | 1/.0005 |
| | | 120 | 0.03 | 1.01 | 1/.0003 |
| | 48 hrs | 120 | — | — | — |
| | | — | 3 | — | — |
| | | 21 | 2 | 0.84 | 1/.0952 |
| | | 26 | 2 | 0.88 | 1/.0769 |
| | | 35 | 2 | 0.96 | 1/.0571 |
| | | 44 | 2 | 1.03 | 1/.0455 |
| | | 80 | 1 | 1.00 | 1/.0125 |
| | | 120 | 0.125 | 1.04 | 1/.001 |
| | | 120 | 0.06 | 1.02 | 1/.0005 |
| | | 120 | 0.03 | 1.01 | 1/.0003 |
| S. aureus ATCC#6538 | 24 hrs | 80 | — | — | — |
| | | — | 0.5 | — | — |
| | | 35 | 0.25 | 0.94 | 1/.0071 |
| | | 44 | 0.25 | 1.05 | 1/.0057 |
| | | 80 | 0.03 | 1.06 | 1/.0004 |
| | | 80 | 0.015 | 1.03 | 1/.0002 |
| | | 80 | 0.007 | 1.01 | 1/.0001 |
| | | 80 | 0.003 | 1.01 | 1/.00003 |
| | | 80 | 0.0015 | 1.00 | 1/.00002 |
| | 48 hrs | 200 | — | — | — |
| | | — | 0.5 | — | — |
| | | 80 | 0.25 | 0.90 | 1/.0031 |
| | | 120 | 0.25 | 1.10 | 1/.0021 |
| | | 80 | 0.06 | 0.52 | 1/.0008 |
| | | 120 | 0.06 | 0.72 | 1/.0005 |
| | | 170 | 0.06 | 0.97 | 1/.0004 |
| | | 210 | 0.06 | 1.17 | 1/.0003 |
| | | 80 | 0.03 | 0.46 | 1/.0004 |
| | | 120 | 0.03 | 0.66 | 1/.0003 |
| | | 170 | 0.03 | 0.91 | 1/.0002 |
| | | 210 | 0.03 | 1.11 | 1/.0001 |
| | | 200 | 0.015 | 1.03 | 1/.0001 |

Ca: component in ppm AI of Cu-MEA(Monoethanolamine complex of copper carbonate)
Cb: component in ppm AI of DCOIT

TABLE 2

| Test Organisms | Contact Time | Ca | Cb | S.I. | Ca/Cb |
|---|---|---|---|---|---|
| A. niger ATCC # 16404 | 3 days | 0.0875 | — | — | — |
| | | — | 750 | — | — |
| | | 0.004 | 500 | 0.71 | 1/125,000 |
| | | 0.02 | 500 | 0.90 | 1/25,000 |
| | | 0.03 | 500 | 1.01 | 1/16,667 |
| | | 0.0525 | 250 | 0.93 | 1/4,762 |
| | | 0.065 | 250 | 1.08 | 1/3,846 |
| | | 0.0525 | 150 | 0.80 | 1/2,857 |
| | | 0.065 | 150 | 0.94 | 1/2,308 |
| | | 0.065 | 75 | 0.84 | 1/1,154 |
| | | 0.0875 | 75 | 1.1 | 1/857 |
| | 7 days | 0.2 | — | — | — |
| | | — | 750 | — | — |
| | | 0.007 | 500 | 0.70 | 1/71,429 |
| | | 0.065 | 500 | 0.99 | 1/7,692 |
| | | 0.065 | 250 | 0.66 | 1/3,846 |
| | | 0.0875 | 250 | 0.77 | 1/2,857 |
| | | 0.11 | 250 | 0.88 | 1/2,273 |
| | | 0.2 | 250 | 1.33 | 1/1,250 |
| | | 0.0525 | 150 | 0.46 | 1/2,857 |
| | | 0.065 | 150 | 0.53 | 1/2,308 |
| | | 0.11 | 150 | 0.75 | 1/1,364 |
| | | 0.2 | 150 | 1.20 | 1/750 |
| | | 0.065 | 75 | 0.43 | 1/1,154 |
| | | 0.11 | 75 | 0.58 | 1/682 |
| | | 0.2 | 75 | 1.08 | 1/375 |
| Ps. aeruginosa ATCC#9027 | 24 hrs | 2 | — | — | — |
| | | — | 250 | — | — |
| | | 0.3 | 150 | 0.75 | 1/500 |
| | | 0.425 | 150 | 0.81 | 1/353 |
| | | 0.65 | 150 | 0.93 | 1/231 |
| | | 0.875 | 150 | 1.04 | 1/171 |
| | | 0.65 | 75 | 0.63 | 1/115 |
| | | 0.875 | 75 | 0.74 | 1/86 |

TABLE 2-continued

| Test Organisms | Contact Time | Ca | Cb | S.I. | Ca/Cb |
|---|---|---|---|---|---|
| | | 1.1 | 75 | 0.85 | 1/68 |
| | | 2 | 75 | 1.30 | 1/37.5 |
| | 48 hrs | 4.25 | — | — | — |
| | | — | 500 | — | — |
| | | 0.425 | 250 | 0.60 | 1/588 |
| | | 0.525 | 250 | 0.62 | 1/476 |
| | | 0.65 | 250 | 0.65 | 1/385 |
| | | 0.875 | 250 | 0.71 | 1/286 |
| | | 1.1 | 250 | 0.76 | 1/227 |
| | | 2 | 250 | 0.97 | 1/125 |
| | | 0.65 | 150 | 0.45 | 1/231 |
| | | 1.1 | 150 | 0.56 | 1/136 |
| | | 2 | 150 | 0.77 | 1/75 |
| | | 3 | 150 | 1.01 | 1/50 |
| S. aureus ATCC#6538 | 24 hrs | 0.65 | — | — | — |
| | | — | 250 | — | — |
| | | 0.002 | 150 | 0.6 | 1/75,000 |
| | | 0.02 | 150 | 0.63 | 1/7,500 |
| | | 0.0525 | 150 | 0.68 | 1/2,857 |
| | | 0.11 | 150 | 0.77 | 1/1,364 |
| | | 0.2 | 150 | 0.91 | 1/750 |
| | | 0.3 | 150 | 1.06 | 1/500 |
| | | 0.0525 | 75 | 0.38 | 1/1,429 |
| | | 0.11 | 75 | 0.47 | 1/682 |
| | | 0.2 | 75 | 0.61 | 1/375 |
| | | 0.425 | 75 | 0.95 | 1/176 |
| | | 0.525 | 75 | 1.11 | 1/143 |
| | | 0.0875 | 50 | 0.33 | 1/571 |
| | | 0.2 | 50 | 0.51 | 1/250 |
| | | 0.525 | 50 | 1.01 | 1/95 |
| | | 0.2 | 25 | 0.41 | 1/125 |
| | | 0.3 | 25 | 0.56 | 1/83 |
| | | 0.425 | 25 | 0.75 | 1/59 |
| | | 0.525 | 25 | 0.91 | 1/48 |
| | | 0.65 | 25 | 1.1 | 1/38 |
| | 48 hrs | 0.65 | — | — | — |
| | | — | 250 | — | — |
| | | 0.002 | 150 | 0.6 | 1/75,000 |
| | | 0.02 | 150 | 0.63 | 1/7,500 |
| | | 0.0525 | 150 | 0.68 | 1/2,857 |
| | | 0.11 | 150 | 0.77 | 1/1,364 |
| | | 0.2 | 150 | 0.91 | 1/750 |
| | | 0.3 | 150 | 1.06 | 1/500 |
| | | 0.0525 | 75 | 0.38 | 1/1,429 |
| | | 0.11 | 75 | 0.47 | 1/682 |
| | | 0.2 | 75 | 0.61 | 1/375 |
| | | 0.425 | 75 | 0.95 | 1/176 |
| | | 0.525 | 75 | 1.11 | 1/143 |
| | | 0.0875 | 50 | 0.33 | 1/571 |
| | | 0.2 | 50 | 0.51 | 1/250 |
| | | 0.525 | 50 | 1.01 | 1/95 |
| | | 0.2 | 25 | 0.41 | 1/125 |
| | | 0.3 | 25 | 0.56 | 1/83 |
| | | 0.425 | 25 | 0.75 | 1/59 |
| | | 0.525 | 25 | 0.91 | 1/48 |
| | | 0.65 | 25 | 1.1 | 1/38 |

Ca: component in ppm AI of DCOIT
Cb: component in ppm AI of Cu(OH)$_2$ (micronized copper)
Ratio: Ca:Cb

The invention claimed is:

1. A synergistic antimicrobial composition comprising:
   (a) 4,5-dichloro-2-n-octyl-4-isothiazolin-3-one; and
   (b) micronized copper;
   wherein a ratio of 4,5-dichloro-2-n-octyl-4-isothiazolin-3-one to micronized copper is from 1:48 to 1:125,000.

2. The synergistic antimicrobial composition of claim 1 in which the ratio of 4,5-dichloro-2-n-octyl-4-isothiazolin-3-one to micronized copper is from 1:59 to 1:125,000.

* * * * *